Figure 1:
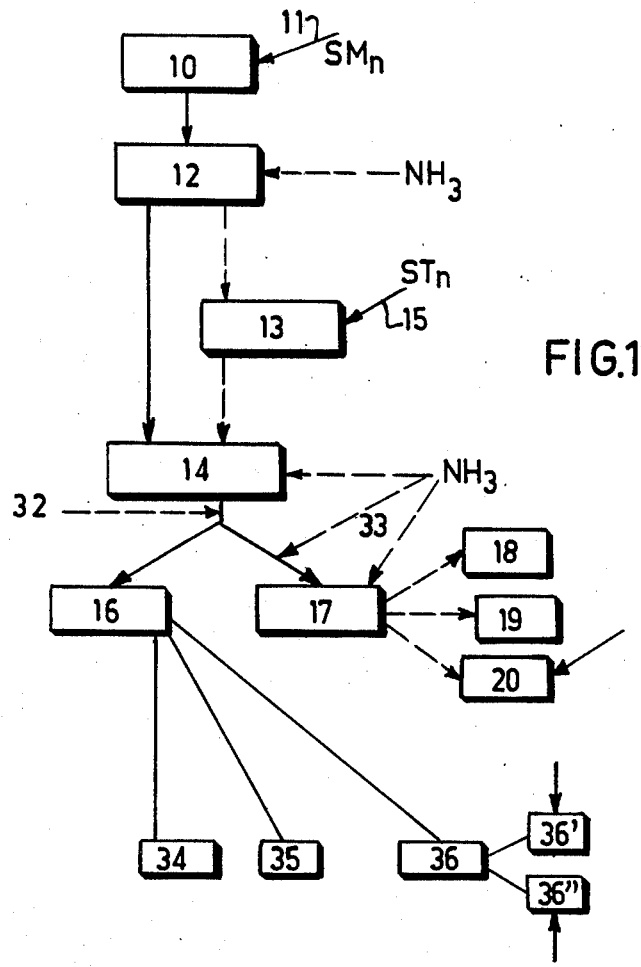

United States Patent [19]

Segard et al.

[11] 4,349,570

[45] Sep. 14, 1982

[54] PROCESS OF TREATING THE JUICE OF SQUEEZED VEGETABLE MATERIAL, SUCH AS LUCERNE, FOR PRODUCING ALIMENTARY PROTEINS AND SUPER-NITROGENATED PROTEIN FOODS, AND PRODUCTS OBTAINED BY SAID PROCESS

[75] Inventors: Emile-Pierre Segard; Jean-Michel Lebeault, both of Villers/Coudon, France

[73] Assignee: Groupement d'Interet Economique Valpron, Compliegne, France

[21] Appl. No.: 120,925

[22] Filed: Feb. 12, 1980

[30] Foreign Application Priority Data

Feb. 16, 1979 [FR] France .................................. 7903951

[51] Int. Cl.$^3$ ............................................... A23K 1/00
[52] U.S. Cl. ......................................... 426/52; 426/51; 426/53; 426/54; 426/61; 426/489; 426/495; 426/636; 426/807
[58] Field of Search ................... 426/489, 495, 49, 61, 426/51, 52, 53, 54, 41, 311, 636, 807; 260/112 R; 435/801; 210/601, 605, 606

[56] References Cited

U.S. PATENT DOCUMENTS

| | | | |
|---|---|---|---|
| 2,600,903 | 6/1952 | Miller | 426/311 |
| 2,982,657 | 5/1961 | Keitel | 426/51 |
| 3,420,676 | 1/1969 | Keitel | 426/51 |
| 3,684,520 | 8/1972 | Bickoff et al. | 426/270 |
| 3,753,723 | 8/1973 | Henderson et al. | 426/49 |
| 3,975,546 | 8/1976 | Stahmann | 426/49 |
| 4,015,018 | 3/1977 | Glabe | 426/54 X |
| 4,066,633 | 1/1978 | Gastineau et al. | 260/112 R |
| 4,070,351 | 1/1978 | Mathan | 260/112 R |
| 4,210,673 | 7/1980 | Kuanta | 426/53 |
| 4,211,798 | 7/1980 | Cater | 426/41 |

FOREIGN PATENT DOCUMENTS 2330328 8/1980 France .
2037614 8/1980 France .

*Primary Examiner*—R. B. Penland
*Attorney, Agent, or Firm*—Y. Judd Azulay

[57] ABSTRACT

The invention relates to a process of treating squeezing juice having a high protein and sugar content, obtained by squeezing vegetable matter to be used as foodstuff. This process comprises the following steps:

submitting said squeezing juice issuing from a squeezing press to a first inoculation with a first mesophile homofermentative lactic bacteria in a proportion of at least $10^4$ bacteria per milliliter;

maintaining the thus inoculated juice at a temperature comprised between 28° and 35° C., preferably 30° C., during 15 to 20 hours, under slow agitation and without aeration, so as to obtain a suspension constituted by an insoluble fraction of vegetable and microbial proteins, and a residual liquid phase, said suspension having a pH comprised between 4.2 and 4.5;

separating said soluble fraction from said liquid fraction; and separately treating the residual liquid and said insoluble fraction.

15 Claims, 2 Drawing Figures

PROCESS OF TREATING THE JUICE OF SQUEEZED VEGETABLE MATERIAL, SUCH AS LUCERNE, FOR PRODUCING ALIMENTARY PROTEINS AND SUPER-NITROGENATED PROTEIN FOODS, AND PRODUCTS OBTAINED BY SAID PROCESS

BACKGROUND OF THE INVENTION

The present invention is related to a process of treating the juice of squeezed vegetable material, especially lucerne, various leguminous plants and pulps, used as fodder, with a view to producing alimentary proteins and super-nitrogenated protein food. The invention is also related to the products obtained by carrying out the above-mentioned process.

For about twenty years, it has been current practice to dehydrate various agricultural products adapted to be used as fodder (such as pulps, lucerne and various leguminous plants), by means of various industrial processes which all were based on directly drying the fodder in an oven, and more particularly in a rotary oven. These installations consume a considerable amount of fuel (about 0.3 ton per ton of final product) and involve high thermal or calorific losses. On account of the recent increase of the cost of petrol-based products, these conventional installations are no longer advantageous from the economical point of view. Recently developed processes endeavour to improve the rentability of dehydration by providing a supplementary treatment stage comprising squeezing of the vegetable matter, so as to reduce the amount of water to be eliminated in the oven. This allows the cost of dehydration to be considerably reduced, however such process involves the production of important amounts of squeezing juice (for example about 500 kg per ton fresh lucerne), resulting in losses of proteins and sugars, which are extracted from the squeezed vegetable matter together with the juice.

In the present description and in the claims by "squeezing juice" is meant "any juice resulting from the squeezing of vegetable material". Furthermore, by "medium" is meant the corresponding "culture medium" or "treatment medium".

Various methods have been disclosed for recovering the proteins from such squeezing juice, especially by thermo-coagulation by means of calories recovered from the dehyration oven.

These known processes allow about 50% of the energy to be recovered, as regards the operating cost. However these processes involve considerable investment, as they comprise complex operations that complicate to an important degree the carrying out of such processes in practice. Furthermore the standardization of the specifications concerning the recovered proteins stemming from the treated squeezing juice raises difficult problems.

Also, the above-mentioned known processes involve the requirement of perfectly controlling the squeezing conditions; it was found, in particular, that the squeezing of the vegetable matter must not be carried too far when it was desired to achieve a satisfactory recovery of the proteins carried off by the juice. More particularly it was found that it was necessary to produce a residual cake having a dry matter content of not more than 12% to 15%, with a view to achieving a satisfactory global balance. According to present knowledge it appears that when the vegetable matter is submitted to supersqueezing, so as to produce cakes having a dry matter content of up to 30 to 35%, such cake, as squeezed, have a comparatively low protein content which leads, in the final treatment stage, to producing pellets, the composition of which differs from the composition of the pellets obtained when conventional dehydration methods are applied. Furthermore it becomes increasingly difficult to recover by thermocoagulation the increasing amounts of proteins carried along by the juice. The energetic gain resulting from dehydration by supersqueezing thus is at least partly counterbalanced by quality loss and by a poor global balance of the recovered substances. It should be noted, too, that the supersqueezing method, while being advantageous as regards the energy consumption and cost involved in dehydrating the squeezing cake, leads to producing important amounts of juice (75,000 m$^3$ juice in an average size unit of a capacity of 40 tons/hour treating 150,000 tons lucerne per campaign). The juice resulting from supersqueezing contains, amongst other constituents, a high amount of organic substances (especially proteins and sugars), so that such juice cannot be rejected directly into a river, on account of its elevated BOD value. It is thus necessary to be able to recover these organic substances prior to discarding the juice in the form of waste material. The thermocoagulation treatment allows only part of these substances (coagulable proteins) to be recovered. Furthermore, on account of the high volumes involved, the juice thus produced must be stocked in important quantities; however these juices are most unstable and highly fermentable. It is thus necessary to be able to stabilize the same, either by refrigeration (which is very expensive) or by adding bacteriostatic and fungiostatic agents, which is also a most expensive method, raising furthermore complex problems as regards consecutive toxicity risks of the thus recovered products. Consequently these approaches are not acceptable from an economical point of view.

The present invention has for its main object to provide a process for treating squeeze juice obtained by squeezing vegetable fodder material, which allows the following advantageous effects to be obtained:

(1) stabilizing the juice (thus avoiding undesirable fermentation phenomena), (2) insolubilizing the proteins (i.e. render said proteins insoluble), (3) increasing the protein content by producing a biomass which can be consumed by animals, (4) obtaining by-products constituted by mineral compounds having a high nitrogen content which can be used as fertilizers and as alimentary (or nutritive) additives, (5) producing a residual effluent which can be rejected into a river and the BOD and COD values of which are acceptable for the natural environment.

The process of treating squeezing juice according to the present invention comprises:

submitting the juice issuing from a squeezing press to a first inoculation with a first mixture of mesophile homofermentative lactic bacteria in an amount of at least 10$^4$ bacteria per milliliter;

maintaining the thus inoculated juice at a temperature of 28° to 35° C., preferably 30° C., during 15 to 20 hours, under slow stirring and without aerating, so as to obtain a suspension constituted by an insoluble fraction of vegetable proteins and microbial proteins, and a residual liquid phase, said suspension having a pH of 4.2 to 4.5;

separating said insoluble fraction from said liquid phase; and treating separately the residual liquid and said insoluble phase.

In one embodiment of the process according to the invention, the suspension is submitted, prior to the step of separating said insoluble fraction from said liquid phase, to a second inoculation using a second mixture of thermophile homofermentative lactic bacteria in an amount of $10^4$ germs per milliliter per 10 cubic meters suspension, the thus inoculated suspension being maintained at a temperature of 40° to 50° C., preferably 45° C., during 18 to 20 hours, the final suspension thus obtained having a pH of 3.3 to 3.6

Broadly speaking the process according to the invention is based on the rapid growth of lactic bacteria directly promoted by the sugars present in the heterogeneous media. Said process then allows lactic acid and/or ammonium lactate to be obtained by a succession of operating phases or stages involving an evolution of the pH of the medium, as will be described herein-below.

The invention will be described herein-below in a more detailed manner with reference to the appended drawing which is given by way of illustration, but not of limitation.

FIG. 1 is a diagram which schematically illustrates the various phases of the process according to the invention.

Figure 2:
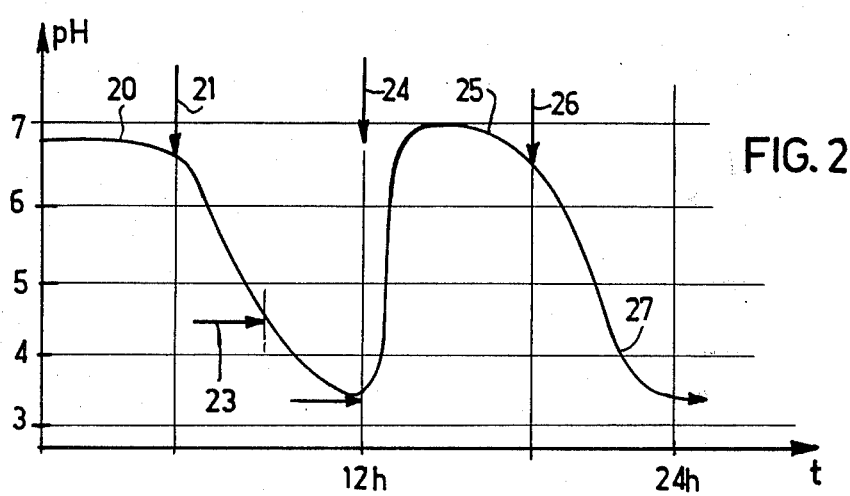

FIG. 2 schematically shows the evolution of the pH, which allows to cause the proteins initially present in the medium to precipitate, and ammonium lactate to be produced.

In the following description the process according to the invention will be illustrated in its applications to lucerne, and several variants allowing certain phases of the process to be omitted will be disclosed there-in.

It should be well understood that the process according to the invention can, of course, also be applied to other natural products, pulps or leguminous plants, such as clover or ray-grass, as well as to various kinds of early or forced vegetables or fruit and their solid waste or scraps, and also, in a general way, to any solution containing sugars and proteins, up to 30% dry matter which stems from squeezing or supersqueezing operations carried out on various vegetable substances, or from various residual media obtained in the food products industry, such as lactoserum.

The process according to the invention is carried out as illustrated in FIG. 1 and comprises, substantially, a first inoculating step wherein the juice to be treated is inoculated, at 10, with a first mixture of bacteria $SM_n$ introduced through 11; this inoculating step is followed by a first storing step at 12 wherein the inoculated juice is maintained at a temperature of about 30° C. According to the invention, a second inoculating step may also be carried out, indicated at 13, using a second mixture of bacteria $ST_n$ introduced through 15, with an addition of ammonia, this second inoculating step being followed by a second storing step 14 wherein the temperature is maintained at about 45° C. The adding of ammonia may be performed in various manners; e.g.:

continuous addition at 12 and 14 with continuous neutralization;

batchwise at 22 when the juice has issued from the storage 14, prior to the separation of phase 16 and 17;

batchwise by addition at 33 after the separation of phases 16 and 17.

It is also possible to proceed with the second storing step immediately after the first one. The second storing step is followed by a separation step by which an insoluble fraction 16 is obtained, said fraction being treated in a consecutive stage indicated at 34 (drying in an oven together with the squeezing cake), at 35 (drying in an oven separately from the cake) and at 36 (wet treatment, at 36', treatment by means of a powderous additive for direct ensilaging, or at 36", treatment by means of a liquid additive so as to produce liquid fodder), whereas a liquid fraction 17 is also treated consecutively at 18-19.

The process according to the invention is based substantially on a rapid growth of lactic bacteria directly from sugars present in the heterogenous media. This process consists in associating an acidifying fermentation, initiating the precipitation of the proteins and the formation of ammonium lactate, which allows the proteins to be supernitrogenated and the treatment to be terminated on residual sugars by another acidification, and leads to creating conditions adapted to allow the treated material to be directly ensilaged.

The lactic acid and/or ammonium lactate are produced by the steps schematically illustrated in FIG. 2.

The diagram of FIG. 2 shows more particularly the evolution of the pH as a function of time, and allows the precipitation of the initially present proteins and production of ammonium acetate leading to the supernitrogenization of the product to be determined correlatively. First part of the curve in FIG. 2 corresponds to a treatment phase wherein the aerobic bacteria (aerobia) use up the oxygen in the neutral liquid, up to reference line 21 where anaerobic fermentation and formation of lactic acid take place, resulting in a decrease of the pH value. Protein precipitation starts at 23 when the pH tends to reach a value of 4.4–4.2. When the pH reaches values of 3.2 to 3.5, ammonia is added at 24 and formation of ammonium lactate takes place in part 25 of the curve. From part 26 on, lactic acid is produced from the residual sugars. The evolution continues by another acidification which leads at 27 to products adapted to be directly ensilaged.

It will be noted that the whole process can be carried out by starting from the strains which are initially present in the treatment medium, or by adding concentrated bacterial media which allow the various phases of the process to be oriented in a selected favourable manner. Especially in the case of lucerne it is possible, for instance, thus to fractionate the proteins present in the green and white forms, during the acidification phase. It is known indeed that green proteins will precipitate at pH values of 4.2 to 4.4, whereas white proteins will precipitate at pH values of 3.2 to 3.5. Thus, when it is desired to collect separately the two categories of proteins it is easy to carry out an intermediary stage so as to collect proteins at pH 4.2 to 4.4.

The various stages or phases of the process, including their possible variants, are described herein-after.

1—First inoculation, directly in the field where the plants are harvested, either in the tanks used for transporting the squeezing juice (when the fodder is squeezed directly in situ after harvesting), or in the storage tanks in the dehydration plant, by means of a concentrated mixture of micro-organisms, designated herein-after by the symbol $SM_n$, in doses corresponding each, for example, to 10 m³ fresh squeezing juice. It is recommended that the inoculation be effected as soon as possible after the juice has issued from the squeezing press, as this facilitates the adaptation of the micro-organisms to the particular juice to be treated and allows a gain of time to be obtained on the latency period (about 90 minutes) which precedes the proliferation of the micro-organisms. In this respect it is advantageous to perform the squeezing directly in the field and to effect the inoculation in the transport tanks, although this is not imperative as regards the subsequent treatment stages. However stage 2 should be initiated directly without previous inoculation of the squeezing juice.

2—Maintaining during 15 to 20 hours the inoculated juice at a temperature of about 30° C. under slight stirring, for example while storing said juice in closed tanks at the treatment plant; the desired temperature is maintained, for example, by means of the calories recovered from the dehydration oven which is used for producing the pellets from the squeezing cake. The storing of the juice can be performed batchwise in one or more tanks the capacity of which corresponds to the production requirements of the plant. In accordance with one variant of the instant process, one or more tanks the temperature of which is maintained at about 30° (28° to 32° C.) may be used in a continuous manner, the dwelling time being selected so as to meet the conditions herein-above (15 to 20 hours at 30° C.). An installation comprising at least one reservoir can be used in accordance with a conveniently adapted technique known in the field of water treatment.

3—Second inoculation of the storage tank after operating phase 2 hereinabove, using a concentrated mixture of micro-organisms which will be designated hereinafter by the symbol "$ST_n$", while the tank used in phase 2 is heated to a temperature of 45° C. during 18 to 20 hours by means of calories which can be recovered from the dehydrating oven. According to a variant comprising continuous treatment, as specified hereinabove in phase 2, the inoculation may be performed in a predetermined, controlled manner in one or more tanks maintained at a temperature of 45° C., the dwelling time being 10 to 20 hours so that the germ concentration never decreases to less than $10^7$ bacteria par milliliter of culture or treatment medium.

In accordance with another modification of the instant process it may be advantageous to carry out operating phase 3 with continuous control of the pH value in such a manner that the latter is maintained close to neutral, between 6.5 to 7.5, by controlled injection of ammonia provided from an auxiliary tank containing liquid ammonia. The frigories provided by ammonia injection will be compensated by the calories recovered from dehydration oven. This operating mode under constant pH conditions can only be applied in phase 3, it being well understood that the acid pH obtained by microbiological action in phase 2 will have been sufficient to inhibit by competition the growth of harmful microbial strains possibly present in the starting juice. This operating mode under constant pH conditions can only be applied when performing in phase 4 hereinbelow the variant involving recovery of the proteins by thermocoagulation. Phase 3 may be omitted by prolonging phase 2, when it is not desired to isolate separately the green proteins from the white proteins. When these two categories of proteins are to be separated, operating phase 2 is discontinued as soon as the pH has reached a value of 4.2 to 4.4; in this case, the insoluble substances (green proteins) are isolated prior to proceeding to another reservoir, in the subsequent stage described in phase 3, whether concentrated bacterial mixtures of the $ST_n$ type are inoculated or not.

4—When leaving the tank at 45° C., as described in phase 3 herein-above, or as soon as the pH has reached a value of 3.3 to 3.6 (in the case where only operating phase 2, but not operating phase 3 is performed), the juice may be treated in accordance with various variants as set forth herein-below.

When the operating phase is performed without continuous neutralization by means of ammonia, the final pH of the juice issuing from the tank in operating phase 3 must not exceed 3.5.

If this value is not obtained spontaneously after a dwelling period of 20 hours at 45° C., it may be advantageous to adjust the final pH of the outflowing juice to a value not lower than 3.3. In all circumstances the extreme values of the pH of the juice issuing from the tank at 45° C. should be comprised between 3.3 (minimum) and 3.6 (maximum). These conditions correspond to the iso-electric precipitation point of the so-called "white proteins"; the so-called "green proteins" will have precipitated previously during operating phase 2, at 30° C., at pH values which may be comprised between 4.5 and 4.8 (iso-electric precipitation point of green proteins).

When it is desired to separate the green proteins from the white proteins it is thus recommended, in accordance with another variant of the instant process, to perform a decantation or centrifugation operation between operating phases 2 and 3 so as to isolate the green proteins precipitated during phase 2 under the acidifying action of the micro-organisms present in the $SM_n$ product.

When the juice has left the tank after performing phase 3—whether the green proteins had been separated or not after performing phase 2—the insoluble fraction is isolated (by continuous centrifugation or decantation), which fraction is constituted by the proteins initially present in the starting juice (green proteins, white proteins, or a mixture of green and white proteins, depending on the particular conditions) in addition to the biomass produced by the fermentation of the sugars of the starting juice. It may be advantageous, with a view to increasing the precipitation efficiency of the total proteins obtained, to adjust the temperature of the juice resulting from phase 3 the pH of which is comprised between 3.2 and 3.6, to a value of 85° C. by causing it to flow through a heat exchanger wherein the calories recovered from the dehydration oven are dissipated; this operating phase should be performed prior to the solid matter-liquid matter separation; however it is known that a loss of solubility of the recovered proteins will result from this operation: the insoluble fraction obtained is dried directly by any convenient means, for instance by a fluidization drying method starting from the vapor issuing from the dehydration oven, or by means of a cylinder dryer using the calories recovered from the oven. During this drying operation the temperature of the product should not exceed a maximum value of 60° C. A proteic flour called "TM" is thus obtained, which can advantageously be used in combination with lactoserum and, possibly, in combination with various sorts of straw, so as to constitute foodstuff for animals.

According to another variant of the instant process it may be advantageous to avoid any risk of thermal degradation of the proteins by separating the insoluble fraction from the juice after performing phase 2 to 3, depending on the selected variant; this may be performed:

by rotary filtration using filters with a projecting filter cloth, in accordance with a method currently used for isolating certain biomasses obtained in various fields of the fermentation industry. The resulting filtering product may then advantageously be used directly, in the moist state, for admixture to lactoserum powder or to lactoserum with or without an addition of cellulosic material, such as straw, so as to produce a moist composite foodstuff;

by simple decantation in a decanting reservoir constructed in accordance with techniques similar to those applied in the field of biological water purification;

by using a rotary press or a belt press, after adding an additive, such as starch, with a view to facilitate the agglomeration of the proteins and the micro-organisms. The resulting moist product may be used as indicated in the preceding paragraph.

In the two above-described variants the product obtained in the moist state by filtration on a rotary filter or by squeezing on a press may finally be dried by an operation such as described in the preceding paragraphs.

In all the cases examined herein-above the isolated proteic fractions can be dried in the dehydration oven used for producing the pellets from the squeezing cake. In this latter case, a certain risk of thermal degradation due to the direct dehydration in the oven has to be accepted.

In the variant described in operating phase 3 herein-above wherein a continuous neutralizing operation is performed directly in the tank, at 45° C., the proteic biomass obtained may be increased by converting the sugars of the squeezing juice, which can be performed by suppressing the retro-inhibition caused by the lactic acid producing during the proliferation phase. It is then possible to isolate the proteins by thermocoagulation by means of an exchanger, using a method known per se.

The advantage of the process according to the instant invention, as compared to the above-mentioned known processes, resides in the fact that the novel process allows a higher global protein content to be obtained, since the sum of initial proteins+proteins stemming from biologic conversion of the sugars is isolated. In this variant it is necessary to adjust the neutralized juice obtained after performing operating phase 3 to a pH comprised between 3.3 and 3.6 prior to coagulation at 85° C.

5—The liquid fraction which is recovered as a supernatant fraction when the proteins are isolated as described in operating phase 4 herein above, may be introduced into an intermediary tank provided with neutralizing means using ammonia directly injected from an auxiliary tank containing liquid ammonia. According to another variant, it may be advantageous not to neutralize the medium so as to maintain the product in the form of lactic acid. The medium, neutralized or not, is concentrated 25 times in a double-acting evaporator using the calories recovered from the dehydration oven in which the fodder or the squeezing cakes stemming from said fodder are dehydrated. As regards the concentrated solution, the ammonium lactate content of which is close to saturation.

said solution may be either sold directly in the liquid state; in this case it may advantageously be added directly to the squeezing cake for direct ensilaging, or it may be added to the dehydrated pellets; when the product is in the form of lactic acid the best ensilaging conditions are encountered; when the product is neutralized in the form of ammonium lactate, "supernitrogenized" cake or pellets will be obtained;

or else said solution may be thoroughly dried by means of an atomizer combined with the evaporator, or by any other convenient drying means.

When it is desired to obtain the ammonium lactate in the pure form it can advantageously be crystallized by the addition of a convenient amount of ethanol to the preceding solution.

The resulting product will thus be a liquid or dry raw fraction of ammonium acetate which can be used in known applications (particularly as a nitrogenized constituent of organic fertilizers), or a purified fraction which can be used in known applications where such pure product is desirable. In both cases the ammonium lactate may be added to the isolated proteins, or used as an additive for other dehydrated products (such as pulp or similar products) with a view to increasing in a considerable proportion to the organic nitrogen content of the final products, which content may be as high as 6% $N_2$, as compared to 1.2% to 1.3% $N_2$ in the proteins alone.

6—In one variant, different from, or complementary to, the one described in operating phase 5 herein-above the liquid fraction may advantageously be submitted to a convenient treatment known per se (for example by means of solvents) with a view to isolating the xantophylls present in the juice in an average proportion of 600 mg per kilogramme of initially harvested fresh lucerne. When treating the concentrated fraction obtained in operating phase 5 with ethanol for crystallizing the ammonium lactate, the xantophylls can be recovered directly from the hydro-alcoholic crystallization mother-liquors.

7—The present invention is also directed to the preparation of the microbial concentrates of the type $SM_n$ and $ST_n$ mentioned hereinabove, from total lucerne juice.

These $SM_n$ and $ST_n$ concentrates are prepared under controlled conditions by means of sterilized fermenter operating under pHstat control with continuous neutralization using ammonia. The necessary amount of lucerne juice collected at the beginning of the campaign is carefully filtered so as to eliminate therefrom the insoluble substances present in the juice, and the juice is then stored under sterile conditions in closed tanks, after adding peracetic acid up to a final concentration of 0.1%. When performing the preparation, the sterilized fermenters are filled with lucerne juice stored under the above-described conditions, and 0.01% of a 1% catalyst solution is injected with a view to decomposing the peroxides present in the medium. The content of the fermenter is treated by injecting strains of type $SM_n$ and $ST_n$ with an initial concentration of $10^3$ bacteria per milliliter.

PRODUCTION OF $SM_n$ CONCENTRATES

The fermenter is heated to 30° C. under slow agitation, without air injection, and maintained at a pH value of 7 by means of ammonia. A mixture of at least two convenient strains for the treatment of lucerne, of the species *Lactobacillus Plantarum, Peiodoccus acidilactici* or *Streptococcus lactis* is injected into the container. These homofermentative mesophile strains, which are currently used in the field of cheese production, will grow on the glucides present in the juice so as to form a biomass and produce lactic acid. As is well known in the field of cheese production, the *Streptococcus lactia* constitutes a strain having a high acidification velocity as well as a high proliferation velocity; however the amount of lactic acid produced is comparatively small, and the final pH obtained without neutralization is rarely lower than 4.5. These strains thus are advantageous, as regards a rapid "invasion" of the medium, whereby the existing undesirable random populations are inhibited by competition. Furthermore the high acidification velocity allows the medium to be rapidly brought out of the neutral range which enhances the development of noxious anaerobia.

The Leuconostoc strains whose acidification velocity is lower exhibit, on the contrary, a higher acidification power whereby they are enabled to lower the pH of the medium to values of 3.4 to 3.5. This pH range corresponds to the range of precipitation of the white proteins of lucerne. The presence of such strains thus is desirable for initiating the acidification in the treatment phase at 30° C., as optimum conditions are thus created for obtaining a pH value of 3.5 during the 2 treatment phase using $ST_n$ at 45° C. (thermophile zone). The presence of *Lactobacillus plantarum* which are mesophile bacteria particularly adapted to grow in vegetable media (the case of sauerkraut may be cited as an example) constitutes a desirable precaution with a view to having a micro-organism which is not strongly affected by possibly present inhibiting compounds, particularly as regards vegetable media (especially polyphenol compounds). Finally, such a mixture of strains is advantageous in that it reduces the possible risks of specific lysis by bacteriophages which infect the squeezing juice to be treated. It is also possible to add to the mixture heterofermentative strains such as *Lactobacillus brevis*, *Lactobacillus fermentum* or *Leuconostoc mesenteroides*. It is further possible to add strains having a high oxygen consumption (particularly strains of the Bacillus type) which will enhance the rapid development of the homofermentative strains by eliminating rapidly the oxygen dissolved in the treatment medium (for example *Bacillus Thurigiensis*).

The $SM_n$ type bacterial concentrate is produced in a mixed culture on aseptic lucerne juice by continuous neutralization of the lactic acid formed. It is known indeed that this conversion product inhibits the cellular proliferation by an effect of the feed-back type. Neutralization of the lactic acid produced during the growth phase allows a final bacteria concentration of at least $10^{11}$ bacteria per milliliter to be obtained. The proliferation curve of the biomass is controlled by a pHstat, and fermentation is discontinued as soon as the neutralization curve reaches an ammonia consumption level. The biomass is collected by centrifugation of the Sharpless type. The bacterial regulus is stirred together with an equal amount (by weight) of milk powder. The resulting product is then lyophilized in a proportion of $10^{11}$ bacteria per 10 cubic meters squeezing juice (inoculation with $10^4$/ml).

It will be understood that a plant having a capacity of 40 tons per hour which is to treat 75,000 m³ during 150 days of campaign will produce the required $SM_n$ quantities in a single operation at the beginning of the campaign in a fermenter having a capacity of 10 liters (useful capacity: 7.5 liters).

PRODUCTION OF $ST_n$ CONCENTRATES

The production conditions are identical to those described hereinabove, with the exception of the fermentation temperature which is 45° C. instead of 30° C. The inoculated fermentation promoter is constituted by a mixture of three strains differently typified with respect to the phages, of the *Lactobacillus Helveticus* species. These thermophile bacteria are characterized by the fact that they have the highest acidification capacity, allowing an acidification of up to pH 3.4–3.5 to be obtained. The doses per 10 m³ are prepared with the same concentration and under the same conditions as in the case of the above-described $SM_n$.

The appended Table shows the balance of products of the process according to the invention.

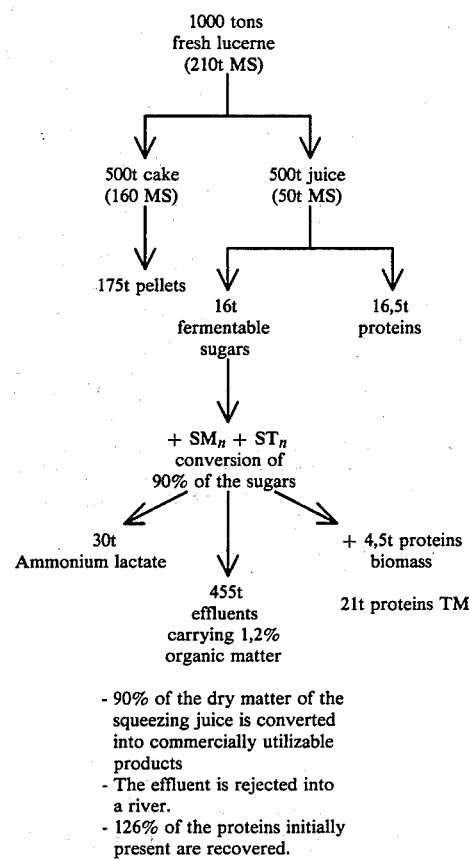

- 90% of the dry matter of the squeezing juice is converted into commercially utilizable products
- The effluent is rejected into a river.
- 126% of the proteins initially present are recovered.

The invention is not limited to the embodiments shown and described herein; various modifications and variants may be envisaged by those skilled in the art within the scope of the invention as defined in the appended claims.

What is claimed is:

1. A process of treating juice having a high protein and sugar content, obtained by squeezing vegetable matter to be used for foodstuff comprising:
   (a) submitting said juice issuing from a squeezing press to a first inoculation with a mesophile homofermentative lactic acid producing bacteria in a proportion of at least $10^4$ bacteria per milliliter, maintaining the inoculated juice at a temperature between 28 and 35 degrees C., during 15 to 20 hours under slow agitation and without aeration, obtaining a suspension of an insoluble fraction of vegetable and microbial proteins and a residual liquid phase, said suspension having a pH between 4.1 and 4.5;

(b) submitting said suspension to a second inoculation with an additional mixture of thermophile homo-fermentative lactic acid producing bacteria in a proportion of $10^4$ bacteria per milliliter per 10 $M^3$ suspension maintaining the inoculated suspension at a temperature of 40 to 50 degrees C., during 18 to 20 hours, the final suspension having a pH of 3.3. to 3.6.

(c) separating said insoluble fraction from said liquid fraction and separately treating the residual liquid and said insoluble fraction, said process being characterized by obtaining a mixture of mesophile homo-fermentative acid producting bacteria from at least two strains of the species, *Streptoccus lactis, Bacillus thurigiensis, Prediococccus acidilactis, Lactobacuillus Plantarum.*

2. The process of claim 1, wherein said additional mixture of thermophile homofermentative lactic acid producing bacteria is constituted by a mixture of three strains differently typified with respect to bacteriophages, said strains being of the species *Lactobacillus Helveticus.*

3. The process of claim 2, wherein the preparation of the inoculated strains of said mixtures of bacteria comprises controlled fermentation on previously filtered and sterilized squeezing juice, at respective temperatures of 30° and 45° C., and a continuous neutralization to a pH value of 7 by means of ammonia, so as to obtain a final concentration of at least $10^{11}$ bacteria per milliliter culture medium.

4. The process of claim 1, wherein after said second inoculation the treatment of the suspension at 45° C. is performed by continuous neutralization at pH 7 by controlled injection of ammonia.

5. The process of claim 1, wherein the separation of the suspension is effected by centrifugation.

6. The process of claim 1, wherein the separation of the suspension is effected by decantation.

7. The process of claim 1, wherein the separation of the suspension is performed after adding starch, adapted to enhance the agglomeration of the proteins and the microorganisms.

8. The process of claim 1, wherein the insoluble fraction is dried to obtain a proteic flour, by fluidization or in a cylinder dryer wherein the temperature in the core of the treated matter does not exceed 60° C.

9. The process of claim 1, wherein said insoluble fraction is stirred in the moist state together with milk powder or dried lactoserum fractions and solid additives, whereafter said insoluble fraction is directly packed in bags for ensilaging during storage by the prolonged action of the lactic bacteria.

10. The process of claim 1, wherein said insoluble fraction is added directly to liquid lactoserum fractions, so as to constitute a liquid composite foodstuff, the lactic bacteria present therein having a prolonged stabilizing effect.

11. The process of claim 1, wherein the residual liquid is neutralized at pH 7, and wherein the resulting neutral solution is concentrated at least 25 times, so as to obtain an ammonium lactate concentration close to saturation.

12. The process of claim 11 wherein ammonium lactate is isolated by crystallizing the concentrated solution by adding ethanol thereto, while xantophylls are obtained from the mother liquor to be obtained by solvents or other liquids.

13. The process of claim 1, wherein said residual liquid is added directly to (the) a squeezing cake comprising said squeezed vegetable matter so that supernitrogenated pellets are obtained after neutralization.

14. The process of claim 1, wherein said residual liquid is added directly to (the) dehydrated pellets produced from said squeezing cake so that supernitrogenated pellets are obtained after neutralization.

15. The process of claim 1, wherein at least part of the heat required for treating of said juice is provided by using the heat dissipated by a dehydration oven used for dehydrating the vegetable matter.

* * * * *